(12) United States Patent
Cathier et al.

(10) Patent No.: US 10,602,959 B2
(45) Date of Patent: Mar. 31, 2020

(54) POSITION DETERMINATION APPARATUS

(71) Applicant: KONINKLIJKE PHILIPS N.V., Eindhoven (NL)

(72) Inventors: Pascal Yves Francois Cathier, Asnières-sur-Seine (FR); Olivier Pierre Nempont, Suresnes (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 841 days.

(21) Appl. No.: 14/646,490

(22) PCT Filed: Dec. 11, 2013

(86) PCT No.: PCT/IB2013/060798
§ 371 (c)(1),
(2) Date: May 21, 2015

(87) PCT Pub. No.: WO2014/091418
PCT Pub. Date: Jun. 19, 2014

(65) Prior Publication Data
US 2015/0272472 A1    Oct. 1, 2015

Related U.S. Application Data

(60) Provisional application No. 61/737,128, filed on Dec. 11, 2013.

(51) Int. Cl.
*A61B 5/06* (2006.01)
*A61B 34/20* (2016.01)
*A61B 34/10* (2016.01)

(52) U.S. Cl.
CPC .............. *A61B 5/064* (2013.01); *A61B 34/20* (2016.02); *A61B 2034/105* (2016.02); *A61B 2034/2055* (2016.02); *A61B 2034/2061* (2016.02)

(58) Field of Classification Search
CPC . A61B 5/064; A61B 34/20; A61B 2034/2055; A61B 2034/105; A61B 2034/2061
See application file for complete search history.

(56) References Cited

U.S. PATENT DOCUMENTS 6,266,552 B1   7/2001  Slettenmark
6,298,261 B1  10/2001  Alexander
(Continued)

FOREIGN PATENT DOCUMENTS

| JP | 2010012097 A | 1/2010 |
| JP | 2010096773 A | 4/2010 |
| JP | 2014504917 A | 2/2014 |

*Primary Examiner* — Bo Joseph Peng

(57) ABSTRACT

A position determination apparatus for determining the position of a working element arranged within an object having an inner structure with respect to a model of the object. The position and shape of a registration element within the inner structure of the object are provided and used for determining a transformation relating the inner structure of the model and the position and shape of the registration element with respect to each other, wherein the position of the working element with respect to the model is determined depending on a provided spatial relation between the working element and the registration element and the determined transformation.

11 Claims, 3 Drawing Sheets

(56) References Cited

U.S. PATENT DOCUMENTS

| | | |
|---|---|---|
| 6,813,512 B2 | 11/2004 | Aldefeld et al. |
| 7,618,374 B2 | 11/2009 | Barnes et al. |
| 7,772,541 B2 | 8/2010 | Duncan et al. |
| 8,050,523 B2 | 11/2011 | Ramamurthy et al. |
| 8,141,558 B2 | 3/2012 | Govari |
| 8,818,143 B2 | 8/2014 | Younge et al. |
| 9,142,015 B2 | 9/2015 | Cathier et al. |
| 2002/0077546 A1 | 6/2002 | Aldefeld et al. |
| 2005/0085714 A1* | 4/2005 | Foley ............... A61B 17/1735 600/424 |
| 2005/0182319 A1* | 8/2005 | Glossop ............... A61B 5/061 600/424 |
| 2006/0074319 A1 | 4/2006 | Barnes et al. |
| 2008/0221425 A1 | 9/2008 | Olson et al. |
| 2009/0137952 A1 | 5/2009 | Ramamurthy et al. |
| 2010/0030063 A1 | 2/2010 | Cinbis et al. |
| 2010/0249506 A1 | 9/2010 | Prisco |
| 2011/0160571 A1 | 6/2011 | Cohen |
| 2011/0308536 A1 | 12/2011 | Govari |
| 2012/0157825 A1 | 6/2012 | Koyrakh et al. |
| 2012/0172724 A1 | 7/2012 | Chung et al. |
| 2013/0150732 A1 | 6/2013 | Manzke et al. |
| 2013/0253312 A1 | 9/2013 | Sato et al. |
| 2013/0310685 A1 | 11/2013 | 'T Hooft et al. |
| 2014/0023250 A1 | 1/2014 | Cathier et al. |

\* cited by examiner

POSITION DETERMINATION APPARATUS

CROSS-REFERENCE TO PRIOR APPLICATIONS

This application is the U.S. National Phase application under 35 U.S.C. § 371 of International Application Serial No. PCT/IB2013/060798, filed on Dec. 11, 2013, which claims the benefit of U.S. Application Ser. No. 61/737,128, filed on Dec. 14, 2012. These applications are hereby incorporated by reference herein.

FIELD OF THE INVENTION

The invention relates to a position determination apparatus, a position determination method and a computer program for determining the position of a working element, which is arranged within an object having an inner structure, with respect to a model of the object. The invention relates further to an interventional system comprising the position determination apparatus.

BACKGROUND OF THE INVENTION

During an interventional procedure a catheter may be moved to a desired location within a person under guidance of two-dimensional x-ray projection images of the person, i.e. interventional images acquired during the interventional procedure, and a pre-interventional three-dimensional image of the person, which may be a raw image or a processed image showing segmented parts of the person and which has been acquired before the interventional procedure. In order to determine the current position of the catheter, the interventional x-ray projection images showing the current position of the catheter and the pre-interventional image can be registered with respect to each other and an overlay of the registered interventional and pre-interventional images can be shown on a display. Thus, for determining the current position of the catheter, i.e. for showing the current position of the catheter within the pre-interventional three-dimensional image of the person, x-rays have to be applied to the person.

SUMMARY OF THE INVENTION

It is an object of the present invention to provide a position determination apparatus, a position determination method and a computer program for determining the position of a working element, which is arranged within an object having an inner structure, with respect to a model of the object, wherein the position of the working element can be determined without necessarily applying x-rays to the object. It is a further object of the present invention to provide an interventional system comprising the position determination apparatus.

In a first aspect of the present invention a position determination apparatus for determining the position of a working element, which is arranged within an object having an inner structure, with respect to a model of the object is presented, wherein the position determination apparatus comprises:

a position and shape providing unit for providing the position and shape of a registration element within the inner structure of the object and a spatial relation between the working element and the registration element, a model providing unit for providing the model of the object, a transformation determination unit for determining a transformation relating the inner structure of the model and the position and shape of the registration element with respect to each other such that the inner structure of the model corresponds to the provided position and shape of the registration element, and a position determination unit for determining the position of the working element with respect to the model depending on the spatial relation between the working element and the registration element and the determined transformation.

Since the determination of the position of the working element just needs a) the transformation relating the inner structure of the model and the provided position and shape of the registration element with respect to each other such that the inner structure of the model corresponds to the provided position and shape of the registration element and b) the provided spatial relation between the working element and the registration element, the position of the working element with respect to the model of the object can be determined without necessarily requiring x-ray projection images showing the working element and, thus, without necessarily applying x-rays to the object.

The working element may be any element, which can be used for influencing an inner part of the object. For instance, the working element can be a catheter, a needle or another interventional tool. The object is preferentially an inner part of a living being like a person or an animal. For instance, the object can be an organ like the heart.

The model of the object can be an image of the object, which preferentially has been generated, before the working element and the registration element have been introduced into the object, and in which the inner structure of the object has been identified. In particular, the model can be a segmented image of the object, wherein parts of the object are segmented within this image for providing the model. The model is, for instance, a cardiac model representing different parts of a heart. The model is preferentially a three-dimensional spatial model. However, the model can also additionally account for a movement of the object, in particular for a periodic movement of the object, i.e. the model can also be a four-dimensional model.

The inner structure can be any inner structure, which is shown by the model and in which the registration element can be introduced. For instance, if the object is the heart of a person, the inner structure may be the aortic root, the ostia of the pulmonary veins, the coronary sinus, et cetera. The registration element may be any element, which can be introduced into the respective inner structure. For instance, the registration element can be a catheter, a needle or another interventional tool that can be introduced into the respective inner structure. Preferentially, the registration element is a substantially longish element like the mentioned catheter.

It is preferred that the position and shape providing unit is adapted to provide registration optical shape sensing data for the registration element for providing the position and shape of the registration element and working optical shape sensing data for the working element for providing the position of the working element and optionally also the shape of the working element, wherein the registration optical shape sensing data and the working optical shape sensing data are related to a same reference coordinate system, in order to provide the spatial relation between the working element and the registration element. In particular, the position and shape of the registration element and the position and shape of the working element are determined by the same optical shape sensing system such that these positions and shapes are automatically known in the same reference coordinate system defined by the optical shape sensing system. This allows automatically and relatively easily providing the position and shape of the registration element within the inner structure of the object and simultaneously the spatial relation between the working element and the registration element.

Preferentially, the position and shape providing unit is adapted to provide the position and shape of the registration element and the spatial relation between the registration element and the working element at different times, wherein the transformation determination unit is adapted to determine the transformation relating the inner structure of the model and the position and shape of the registration element with respect to each other for the different times such that the inner structure of the model corresponds to the provided position and shape of the registration element at the different times, and wherein the position determination unit is adapted to determine the position of the working element with respect to the model at the different times depending on the spatial relation between the working element and the registration element provided for the different time and the transformation determined for the different times. This dynamic, i.e. time-dependent, determination of the position and shape of the registration element, of the spatial relation between the registration element and the working element, of the transformation relating the inner structure of the model and the position and the shape of the registration element with respect to each other and of the position of the working element with respect to the model allows for an accurate determination of the position of the working element within the model, even if the object is a moving object like the heart of a person, because due to this dynamic approach the movement, which may be a combination of respiratory and cardiac motion, can be inherently considered. In particular, this dynamic approach may allow for a real-time determination of the position of the working element with respect to the model.

In a preferred embodiment, the transformation determination unit is adapted to determine a rigid transformation. Particularly, the transformation determination unit is adapted to determine a rigid translation. If the transformation is a rigid transformation, the determination of the position of the working element with respect to the model can be more robust. However, the transformation determination unit can also be adapted to determine a non-rigid transformation.

In a further aspect of the present invention an interventional system is presented, wherein the interventional system comprises:
 a working element for being introduced into an object for influencing the object,
 a registration element for being introduced into an inner structure of the object, and
 a position determination apparatus for determining the position of the working element with respect to a model of the object as defined in claim 1.

In a further aspect of the present invention a position determination method for determining the position of a working element, which is arranged within an object having an inner structure, with respect to a model of the object is presented, wherein the position determination method comprises:
 providing the position and shape of a registration element within the inner structure of the object and a spatial relation between the working element and the registration element by a position and shape providing unit,
 providing the model of the object by a model providing unit,
 determining a transformation relating the inner structure of the model and the position and shape of the registration element with respect to each other such that the inner structure of the model corresponds to the provided position and shape of the registration element by a transformation determination unit, and
 determining the position of the working element with respect to the model depending on the spatial relation between the working element and the registration element and the determined transformation by a position determination unit.

In a further aspect of the present invention a computer program for determining the position of a working element, which is arranged within an object having an inner structure, with respect to a model of the object is presented, wherein the computer program comprises program code means for causing a position determination apparatus as defined in claim 1 to carry out the steps of the position determination method defined in claim 10, when the computer program is run on a computer controlling the position determination apparatus.

It shall be understood that the position determination apparatus of claim 1, the interventional system of claim 9, the position determination method of claim 10, and the computer program of claim 11 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
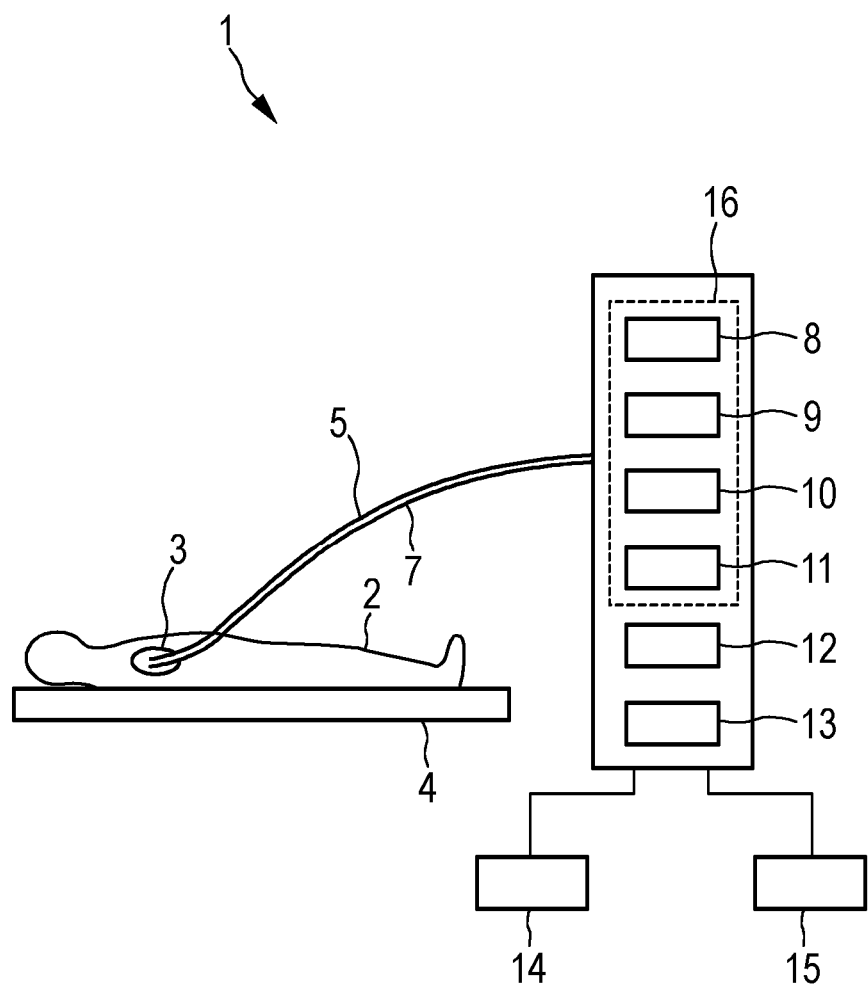
FIG. 1 shows schematically and exemplarily an embodiment of an interventional system.

FIG. 1 shows schematically and exemplarily an interventional system 1 for performing a catheter procedure. The interventional system 1 comprises a working catheter 5 and a registration catheter 7, which are both introduced into the heart 3 of a person 2 lying on a support means like a patient table 4. The working catheter 5 and the registration catheter 7 are connected to a position and shape providing unit 8, wherein this position and shape providing unit 8 and the working and registration catheters 5, 7 are adapted to determine the position and shape of the working and registration catheters 5, 7 by optical shape sensing. For this optical shape sensing known optical shape sensing techniques can be used like the technique disclosed in U.S. Pat. No. 8,050,523 B2.

The positions and shapes of the working catheter 5 and the registration catheter 7 are determined within the same reference coordinate system such that the position and shape providing unit 8 can not only provide the positions and shapes of the working and registration catheters 5, 7, but also simultaneously the spatial relation between the working catheter 5 and the registration catheter 7.

The interventional system 1 further comprises a model providing unit 9 for providing a model of the heart 3, i.e. for providing a cardiac model. The model shows the anatomy of the heart 3, i.e. the positions and shapes of the different parts of the heart 3, wherein the model has preferentially been determined based on a pre-interventional volumetric scan like a computed tomography scan or a magnetic resonance imaging scan, which results in a volumetric image of the heart 3, which has been segmented and labeled. Particularly, an anatomy of interest within the heart 3, at which the working catheter 5 should influence the heart 3, is segmented and labeled in the final model of the heart 3. The model of the heart 3 can be a model of the entire heart or of a part of the heart. For instance, the model can be a model of the aortic root, the left atrium, et cetera. The model providing unit 9 is preferentially a storing unit, in which the pre-interventionally generated model is stored and from which the model can be retrieved during an interventional procedure for providing the same.

The interventional system 1 further comprises a transformation determination unit 10 for determining a transformation relating the inner structure of the model and the position and shape of the registration catheter 7 with respect to each other such that the inner structure of the model corresponds to the provided position and shape of the registration catheter 7. Thus, in this embodiment the cardiac model is transformed such that the position and shape of an anatomical structure of the heart 3, which is the inner structure in this embodiment, match the position and shape of the registration catheter 7, which may also be regarded as being an anatomy catheter, arranged within the anatomical structure.

If the model comprises several inner structures, in which the registration catheter 7 could be introduced, the transformation determination unit 10 can automatically determine, in which inner structure the registration catheter 7 has been introduced based on the position and shape of the registration catheter 7 within the heart 3. For instance, assignments between possible shapes of the registration catheter 7 and the inner structures can be provided, wherein based on these assignments and an actually determined shape of the registration catheter 7 it can be determined, in which inner structure the registration catheter 7 has been introduced. However, generally a user like a physician knows, in which inner structure the registration catheter 7 has been introduced, such that alternatively this knowledge can be input to the interventional system 1 via an input unit 14 like a keyboard, a mouse, a touchpad, et cetera and can be used by the transformation determination unit 10 for determining the transformation. Thus, optionally the knowledge of the part of the anatomy, in which the registration catheter 7 has been stuck in, can be used for determining the transformation.

The matching between the position and shape of the registration catheter 7 and the corresponding inner structure of the model is preferentially a rigid translation of the model of the object. However, also another rigid transformation or even a non-rigid transformation can be used for matching the inner structure of the object 3 and the position and shape of the registration catheter 7 with respect to each other.

The position and shape providing unit 8 is preferentially adapted to provide the position and shape of the registration catheter 7 and the spatial relation between the registration catheter 7 and the working catheter 5 at different times, wherein the transformation determination unit 10 is adapted to determine the transformation relating the inner structure of the model and the position and shape of the registration catheter 7 with respect to each other for the different times such that the inner structure of the model corresponds to the provided position and shape of the registration catheter 7 at the different times, and wherein the position determination unit 11 is adapted to determine the position of the working catheter 5 with respect to the model at the different times depending on the spatial relation between the working catheter 5 and the registration catheter 7 provided for the different times and the transformation determined for the different times. The model can therefore four-dimensionally, i.e. spatially and temporally, be adapted to the respective actual position and shape of the registration catheter 7, in order to show the position of the working catheter 5, in particular, of the tip of the working catheter 5, accurately within the model, even if the object 3 is moving object like in the present example of a living heart 3. Thus, the position and shape of the registration catheter 7 can be used to register the model spatially and temporally.

If the position and shape of the registration catheter 7 has been related to the inner structure of the model, the model and the registration catheter 7 are registered with respect to each other. Since the spatial relation between the registration catheter 7 and the working catheter 5 is known from the position and shape providing unit 8, also the working catheter 5 is registered with the model such that the position determination unit 11 can determine the position of the working catheter 5 with respect to the model and this position, in particular, the position of the tip of the working catheter 5, can be shown within the model on a display 15 of the interventional system 1.

Since the position and shape providing unit 8, the model providing unit 9, the transformation determination unit 10 and the position determination unit 11 are used for determining the position of the working catheter 5 with respect to the model of the heart 3, these units can be regarded as being units of a position determination apparatus 16.

Figure 2:
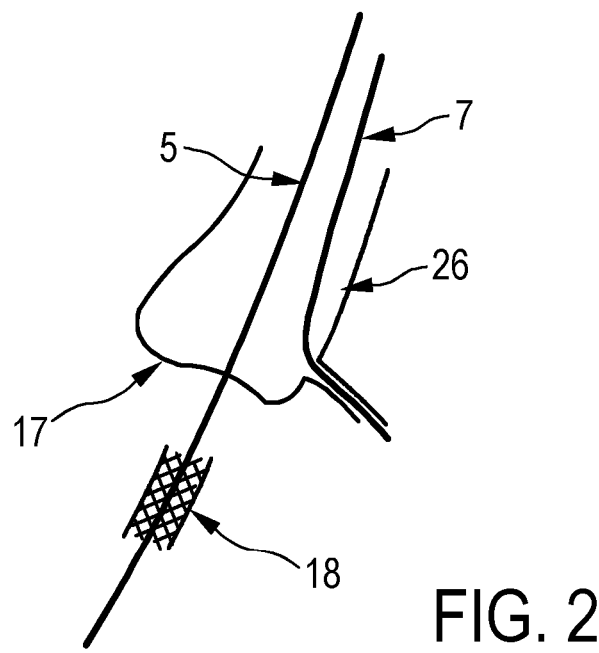
FIG. 2 shows schematically and exemplarily an arrangement of a working catheter and a registration catheter during a transcatheter aortic valve implementation procedure, which may be performed by the interventional system.
Figure 3:
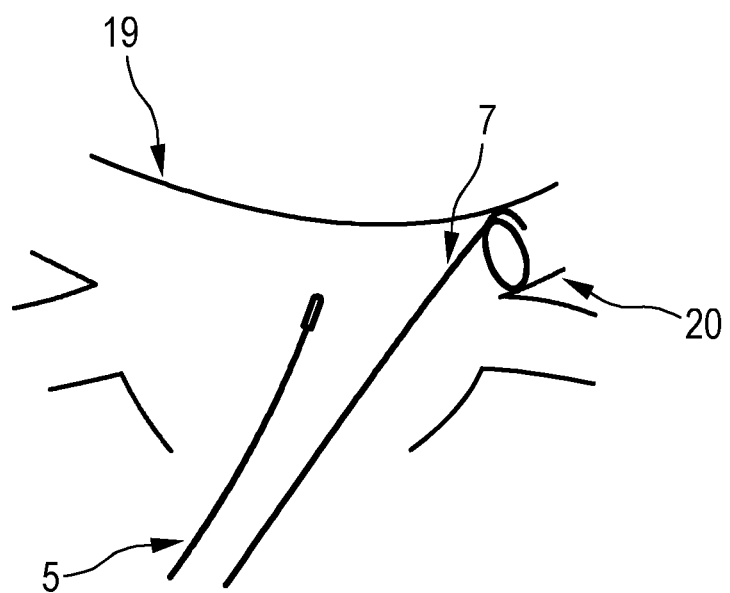
FIG. 3 shows schematically and exemplarily an arrangement of a working catheter and a registration catheter during an atrial fibrillation ablation procedure, which may be performed by the interventional system.

The interventional system 1 can be adapted to perform transcatheter cardiac procedures as will be described in the following with reference to FIGS. 2 and 3.

The interventional system 1 can be adapted to perform a transcatheter aortic valve implementation (TAVI) procedure, wherein the position of an artificial valve 18 is tracked by mounting it on the working catheter 5 being a shape-sensing enabled catheter. In order to relate a position of the artificial valve 18 to the position of the aortic plane 17, where the artificial valve 18 should be deployed, the aortic root 26 is tracked by using the registration catheter 7 being a second shape-sensing enabled catheter introduced into a coronary of the heart 3 as exemplarily and schematically shown in FIG. 2. Optionally, a second registration catheter can be introduced into the other coronary, in order to increase the precision of registering the model of the heart 3 with the registration catheters. The model of the heart 3, which may be a model of the entire heart 3 or, in this case, a model of the aortic bulb of the heart 3 only, is then registered such that the one registration catheter 7 or the two registration catheters, which are arranged within one or two coronaries, respectively, fit inside the coronaries of the model, i.e. a transformation relating one or two coronaries of the model and the position and shapes of the one or two registration catheters, respectively, is determined, wherein this transformation can be used together with the known spatial relation between the one or two registration catheters, respectively, and the working catheter 7 for determining the position of the working catheter 7 and thus of the artificial valve 18 mounted on the working catheter 5 with respect to the provided model.

The interventional system 1 can also be adapted to perform an atrial fibrillation ablation procedure as well in the following exemplarily be described with reference to FIG. 3. In this embodiment, the working catheter 5 is an ablation catheter for ablating cardiac tissue, wherein also in this example the working catheter 5 is tracked by using optical shape-sensing, which allows the position and shape providing unit 8 to provide the position and shape of the working catheter 5. Moreover, in this example the anatomy of interest is the left atrial roof as well as the ostia of the pulmonary veins and more generally the cavity of the left atrium 19, wherein parts of the cavity of the left atrium 19 should be ablated. In this embodiment the model is a model of a part of the heart at least or only including the left atrium 19 with the pulmonary veins 20. Furthermore, in this example the registration catheter 7 is a lasso catheter inserted into the ostia of the pulmonary veins. However, also in this embodiment more than one registration catheter 7, in particular, more than one lasso catheter can be introduced into the ostia of the pulmonary veins. The model can then be adapted such that the segmented pulmonary vein of the model encloses the lasso catheter 7 based on the provided position and shape of the lasso catheter 7, wherein the adapted model can be used together with the known spatial relation between the ablation catheter 5 and the lasso catheter 7 for determining the position of the ablation catheter 5, in particular, of the tip of the ablation catheter 5, within the model.

The interventional system 1 further comprises a navigation unit 12 for allowing the catheters 5, 7, in particular, the tips of the catheters 5, 7, to be navigated to desired locations within the person 2. The navigation unit 12 can be adapted to allow a user like a physician to navigate the catheters 5, 7 completely by hand or semi-automatically. The catheters 5, 7 preferentially comprise built-in guiding means (not shown in FIG. 1), which can be controlled via the navigation unit 12. The catheters 5, 7 can, for example, be steered and navigated by the use of steering wires, in order to guide the tips of the catheters 5, 7 to desired locations within the person 2.

If the working catheter 5 is an ablation catheter as described above with reference to FIG. 3, the interventional system may further comprise an ablation energy source 13 for providing, for instance, radio frequency (RF) energy for ablating the cardiac tissue.

Figure 4:
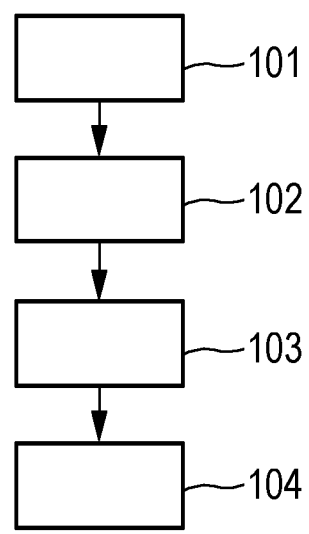
FIG. 4 shows a flowchart exemplarily illustrating an embodiment of a position determination method for determining the position of a working element, which is arranged within an object having an inner structure, with respect to a model of the object.

In the following an embodiment of a position determination method for determining the position of a working element, which is arranged within an object having an inner structure, with respect to a model of the object is exemplarily be described with reference to a flowchart shown in FIG. 4.

In step 101 a model of the object 3 is provided by the model providing unit 9. Particularly, a cardiac model showing parts of the heart 3 of the person 2 is provided, wherein the parts of the heart 3 have been segmented in a three-dimensional image of the heart 3 acquired before the interventional procedure is performed. In step 102 the position and shape of the registration element 7 within the inner structure of the object 3 and a spatial relation between the working element 5 and the registration element 7 are provided by the position and shape providing unit 8. In particular, the position and shape of the registration catheter 7 within the inner structure of the heart 3 and the position and shape of the working catheter 5 within the object 3 are determined by optical shape sensing with respect to the same reference coordinate system, in order to provide the spatial relation between these catheters 5, 7.

In step 103 a transformation relating the inner structure of the model and the position and shape of the registration element 7 with respect to each other is determined such that the inner structure of the model corresponds to the provided position and shape of the registration element 7 by the transformation determination unit 10. For instance, the cardiac model is adapted such that the inner structure of the model encloses the registration catheter, which has been introduced into the inner structure, based on the provided position and shape of the registration catheter 7. In step 104 the position of the working element 5 with respect to the model is determined depending on the spatial relation between the working element 5 and the registration element 7 and the determined transformation by the position determination unit 11.

Steps 101 and 102 can be performed in another sequence, i.e. step 102 can be performed before step 101, or they can be performed simultaneously. Moreover, steps 101 to 104 are preferentially performed during an interventional procedure, in order to allow a user like a physician to perform the interventional procedure based on the determined position of the working element 5 with respect to the model of the object 3. Steps 102 to 104 can be performed continuously in a loop and in real-time, in order to show the position of the working element 5, in particular, of a tip of a working catheter 5, with respect to the model of the object 3 in real-time on the display 15.

The interventional system is preferentially adapted to perform a minimally invasive interventional procedure, in particular a minimally invasive interventional cardiac procedure. The interventional system is preferentially adapted to provide an access to pre-interventionally generated volume images of the person, from which anatomical regions of interest can be extracted, which can be registered to an actual position of the person during the interventional procedure. The registration can be used as a guide or map during the interventional procedure for showing the anatomy of, for instance, the heart of the person, to which the user like an interventionist has not direct visual access during the interventional procedure. For fulfilling this guidance purpose, the registered pre-interventional volume with the segmented anatomical regions of interest, i.e. the model of the object, and the determined position of the respective working element can be shown on the display of the interventional system. Moreover, additional information like calcifications, scars, and other features of the object, of which the positions with respect to the model of the object are known, can be shown on the display together with a representation of the working element. This additional information can be known pre-interventionally or it can be measured during the interventional procedure, wherein in the latter case a catheter with sensing elements for measuring additional information may be used.

The interventional system is preferentially adapted to dynamically determine the position of the working element with respect to the model of the object, in order to account for a possible motion of the object, for instance, in order to account for cardiac motion and breathing motion, which may be present, if the object is a moving heart of a person. The interventional system preferentially continuously, i.e. "online", determines the position of the working element with respect to the model, in order to provide an accurate help at all times.

The interventional system is preferentially adapted to use shape-sensing enabled catheters to register in real-time surgical tools and an anatomy. On the one hand, one or several catheters, i.e. the registration catheters, which can also be regarded as being anatomy catheters, are stuck into anatomical parts that have been segmented previously and that are related to an anatomical region of interest either by a fixed or a known motion. The one or several registration catheters are shape-sensing enabled such that the position and shape of the one or several registration catheters and thus of the anatomical parts, i.e. the internal structures, into which the one or several registration catheters are stuck, can be provided. The model can be adapted such that segmented anatomical parts of the model, which represent the anatomical parts into which the one or several registration catheters are stuck, correspond to the positions and shapes of the one or several registration catheters. The model also comprises a segmented anatomical region of interest, which corresponds to the anatomical region of interest, which should be influenced by the working element, and the model provides a relation between the segmented anatomical parts and the segmented anatomical region of interest. Thus, the relation between the anatomical region of interest and the one or several registration catheters is known, after the model has been adapted to the position and shape of the one or several registration catheters. The relation between the segmented anatomical region of interest and the segmented anatomical parts defined by the model can be a fixed relation or a temporally changing relation, wherein in the latter case it is assumed that the anatomical parts and the anatomical region of interest move with respect to each other. For instance, if a registration catheter has been introduced into the coronary sinus and if the anatomical region of interest is the left atrial roof, the model preferentially provides a temporally changing relation between the coronary sinus and the left atrial roof. For providing such a model considering patient-specific dynamical aspects, a four-dimensional image of the object, in particular, of the heart of the person, can be acquired pre-interventionally and segmented, in order to provide a four-dimensional model relating at least the anatomical parts, in which one or several registration catheters may be introduced, and the anatomical region of interest with respect to each other. The model may be a model of a part of the heart only like a model of simply the left atrium area. For factoring out the heart beat motion of the coronary sinus that the left atrial roof and the pulmonary veins do not experience the interventional system can also be adapted to apply the patient-specific learning technique disclosed in WO 2012/117321 A1.

On the other hand, surgical tools, i.e. working elements, can be tracked by shape-sensing, wherein the position of the working element can be directly given by the position of one or several related shape-sensing fibers of corresponding working catheters. The position of the surgical tool and the position and shape of the one or several registration catheters are preferentially known in the same reference frame, in order to get as a final result a spatial and optionally also temporal relation between the position of the surgical tool and the anatomy of interest, which may be shown on the display of the interventional system. The interventional system therefore provides a registration between the surgical tool and the anatomy based on shape-sensing enabled catheters.

The interventional system is preferentially adapted to track the anatomy and a surgical tool, i.e. a working element, in real-time, wherein the anatomy is tracked in real-time by tracking the position and shape of a registration element introduced into the anatomy such that the registration element moves with the moving anatomy. Moreover, the interventional system may have a built-in ability to factor out rigid body motion like breathing motion as a first approximation and can be extended to handle other sources of motion, in particular, of non-rigid motion, wherein the interventional system can be adapted to use the technique disclosed in WO 2012/117321 A1.

Although in above described embodiments the interventional system is adapted to perform a minimally invasive cardiac procedure, in other embodiments the interventional system can also be adapted to perform another interventional procedure, for instance, an interventional procedure to be applied to another part of a person or an animal like another organ.

The working element can be navigated to a desired location within the object based on the determined position of the working element with respect to the model of the object. The interventional system can be adapted to bypass any need of a pre-interventional x-ray exposure for registering an actual position of a working element within an object with a model of the object, which has been determined based on a pre-interventional image of the object.

Although in the embodiment described above with reference to FIG. 2 the registration catheter is a lasso catheter introduced into the ostia of the pulmonary veins, in another embodiment alternatively or in addition a registration catheter can be introduced into the coronary sinus, wherein, if the registration catheter in the coronary sinus is used for determining a position of the left atrial roof being the anatomical region of interest, the corresponding cardiac model defines the motion between the coronary sinus and the left atrium roof as described above, in order to allow the interventional system to determine the position of the respective working catheter with respect to the position of the left atrium roof.

If the working catheter is an ablation catheter, the interventional system can be adapted to indicate in the model positions, which have been ablated, i.e. to indicate ablation sites. Moreover, if the ablation catheter has an electrical sensing capability for generating activation maps, the electrical values sensed at different locations can be related to the corresponding positions in the model, wherein then the model can be shown together with this additional information on the display of the interventional system.

Although in some above described embodiments the interventional system only comprises a single working element and a single registration element, in particular, a single working catheter and a single registration catheter, the interventional system can generally comprise one or several working elements, in particular, one or several working catheters, and one or several registration elements, in particular, one or several registration catheters.

Although in the above described embodiments the working and registration elements are preferentially working and registration catheters, the working and registration elements can also be other elements, which can be introduced into the object. For instance, the working element and/or the registration element can also be a needle or another interventional tool.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the model of the object, the determination of the transformation relating the inner structure of the model and the position and shape of the registration element with respect to each other, the determination of the position of the working element with respect to the model, et cetera performed by one or several units or devices, can be performed by any other number of units or devices. For example, steps 103 and 104 can be performed by a single unit or by any other number of different units. The procedures and/or the control of the position determination apparatus in accordance with a position determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a position determination apparatus for determining the position of a working element arranged within an object having an inner structure with respect to a model of the object. The position and shape of a registration element within the inner structure of the object are provided and used for determining a transformation relating the inner structure of the model and the position and shape of the registration element with respect to each other, wherein the position of the working element with respect to the model is determined depending on a provided spatial relation between the working element and the registration element and the determined transformation. In this way the position of the working element with respect to the model of the object can be determined without necessarily requiring x-ray projection images showing the working element and, thus, without necessarily applying x-rays to the object.

The invention claimed is:

1. A position determination apparatus adapted to determine a position of a working element arranged within an object having an inner structure, the position being with respect to a model of the object, the position determination apparatus comprising:
   a tangible computer-readable storage that is not a transitory propagating wave or signal configured to provide the model of the object,
   a processor coupled to the storage, the processor
      adapted to provide a position and shape of a registration element within the inner structure of the object and a spatial relation between the working element and the registration element,
      adapted to match the inner structure of the model and the provided position and shape of the registration element with respect to each other such that the inner structure of the model is matched to the provided position and shape of the registration element,
      adapted to determine a transformation based on the match between the inner structure of the model and the provided position and shape of the registration element, wherein the transformation transforms between the inner structure of the model and the provided position and shape of the registration element, and
      adapted to determine the position of the working element with respect to the model depending on the spatial relation between the working element and the registration element and the determined transformation.

2. The position determination apparatus as defined in claim 1, wherein the processor is adapted to determine registration optical shape sensing data from the registration element for providing the position and shape of the registration element and working optical shape sensing data for the working element for providing at least the position of the working element, wherein the registration optical shape sensing data and the working optical shape sensing data are related to a same reference coordinate system, in order to provide the spatial relation between the working element and the registration element.

3. The position determination apparatus as defined in claim 1, wherein the registration element is a registration catheter.

4. The position determination apparatus as defined in claim 1, wherein the processor is adapted to provide the position and shape of the registration element and the spatial relation between the registration element and the working element at different times, is adapted to determine the transformation relating the inner structure of the model and the provided position and shape of the registration element with respect to each other for the different times such that the inner structure of the model corresponds to the provided position and shape of the registration element at the different times, and is adapted to determine the position of the working element with respect to the model at the different times depending on the spatial relation between the working element and the registration element provided for the different times and the transformation determined for the different times.

5. The position determination apparatus as defined in claim 1, wherein the processor is adapted to determine a rigid transformation.

6. The position determination apparatus as defined in claim 1, wherein the memory is adapted to provide a cardiac model as the model.

7. The position determination apparatus as defined in claim 6, wherein the inner structure is the aortic root and the registration element is a registration catheter within the aortic root.

8. The position determination apparatus as defined in claim 6, wherein the inner structure is the ostia of the pulmonary veins and/or the coronary sinus and the registration element is a registration catheter.

9. An interventional system comprising:
   a working element capable of being introduced into an object for influencing the object,
   a registration element capable of being introduced into an inner structure of the object, wherein the registration element is configured to correspond to the inner structure of the object when introduced, and
   a position determination apparatus adapted to determine a position of the working element with respect to the registration element and a model of the object, the position determination apparatus comprising:

a tangible computer-readable storage that is not a transitory propagating wave or signal configured to provide the model of the object, a processor coupled to the storage, the processor adapted to provide a position and shape of the registration element within the inner structure of the object and a spatial relation between the working element and the registration element, adapted to match the inner structure of the model and the provided position and shape of the registration element with respect to each other such that the inner structure of the model is matched to the provided position and shape of the registration element, adapted to determine a transformation based on the match between the inner structure of the model and the provided position and shape of the registration element, wherein the transformation transforms between the inner structure of the model and the provided position and shape of the registration element, and adapted to determine the position of the working element with respect to the model depending on the spatial relation between the working element and the registration element and the determined transformation.

10. A position determination method for determining a position of a working element arranged within an object having an inner structure, with respect to a model of the object, the position determination method comprising acts of:

providing the model of the object, providing a position and shape of a registration element within the inner structure of the object and a spatial relation between the working element and the registration element, matching the inner structure of the model and the provided position and shape of the registration element with respect to each other such that the inner structure of the model is matched to the provided position and shape of the registration element, determining a transformation based on the match between the inner structure of the model and the provided position and shape of the registration element, wherein the transformation transforms between the inner structure of the model and the provided position and shape of the registration element, and determining the position of the working element with respect to the model depending on the spatial relation between the working element and the registration element and the determined transformation.

11. A tangible computer-readable storage that is not a transitory propagating wave or signal, the storage including a computer program for performing the method of claim 10.

* * * * *